US012744118B2

(12) United States Patent
Themelis

(10) Patent No.: US 12,744,118 B2
(45) Date of Patent: Sep. 22, 2026

(54) SYSTEM, METHOD, AND COMPUTER PROGRAM FOR AN IMAGING DEVICE OF A SURGICAL IMAGING SYSTEM

(71) Applicant: Leica Instruments (Singapore) Pte. Ltd., Singapore (SG)

(72) Inventor: George Themelis, Singapore (SG)

(73) Assignee: Leica Instruments (Singapore) Pte Ltd., Singapore (SG)

( * ) Notice: Subject to any disclaimer, the term of this patent is extended or adjusted under 35 U.S.C. 154(b) by 198 days.

(21) Appl. No.: 18/704,985

(22) PCT Filed: Oct. 27, 2022

(86) PCT No.: PCT/EP2022/080049
§ 371 (c)(1),
(2) Date: Apr. 26, 2024

(87) PCT Pub. No.: WO2023/073085
PCT Pub. Date: May 4, 2023

(65) Prior Publication Data

US 2025/0006348 A1 Jan. 2, 2025

(30) Foreign Application Priority Data

Oct. 28, 2021 (EP) .................................... 21205279

(51) Int. Cl.
*G16H 40/00* (2018.01)
*A61B 1/00* (2006.01)
*A61B 90/20* (2016.01)

(52) U.S. Cl.
CPC ......... *G16H 40/00* (2018.01); *A61B 1/00006* (2013.01); *A61B 90/20* (2016.02)

(58) Field of Classification Search
CPC ........................... A61B 1/00006; A61B 90/20; G02B 21/0012; G16H 40/00
See application file for complete search history.

(56) References Cited

U.S. PATENT DOCUMENTS

2009/0182577 A1 7/2009 Squilla et al.
2015/0230715 A1* 8/2015 Nahm ...................... G06T 7/90 600/431
2019/0107700 A1 4/2019 Lee et al.
2019/0110855 A1* 4/2019 Barral ................... A61B 90/37

* cited by examiner

*Primary Examiner* — Scott Luan
(74) *Attorney, Agent, or Firm* — 2SPL Patent Attorneys PartG mbB; Kieran O'Leary

(57) ABSTRACT

Examples relate to a system (110), a method, and a computer program for a imaging device (120) of a surgical imaging system (100), and to a corresponding surgical imaging system comprising such a system. The system is configured to determine a first set of settings being suitable for using the imaging device in a surgical procedure. The system is configured to determine a second set of settings currently being used. The system is configured to provide a signal indicating a difference between the first and second set of settings. The signal comprises information on at least one setting to adjust to obtain the first set of settings.

18 Claims, 2 Drawing Sheets

SYSTEM, METHOD, AND COMPUTER PROGRAM FOR AN IMAGING DEVICE OF A SURGICAL IMAGING SYSTEM

TECHNICAL FIELD

Examples relate to a system, a method, and a computer program for an imaging device of a surgical imaging system, and to a corresponding surgical imaging system comprising such a system.

BACKGROUND

Surgical imaging devices, such as surgical microscopes, endoscopes or exoscopes, are complex imaging systems with multiple user-controlled parameters that can affect the imaging performance. For example, the same field of view can be achieved with different combinations of working distance and magnification. However, a fluorescence sensitivity and an imaging resolution would not be the same for those different settings. As a result, an unexperienced user might end up using the imaging device with suboptimal settings.

Cars, an in particular internal combustion engine-based cars, often show indicators that assist the driver in driving the vehicle, such as instant fuel consumption and the gear to be selected for optical performance. Thereby, the car helps the driver to have better insights regarding the efficiency of the car use (e.g., with respect to fuel consumption), and provides recommendations on how the utilization of the car can be optimized. Such indicators are also known from other systems. For example, digital consumer cameras may show an indicator regarding the lighting conditions, i.e. whether the chosen shutter speed is likely to result in an underexposed or overexposed image.

In general, surgical imaging devices might not provide feedback for the imaging settings. For example, at large working distances (WD) and high magnifications (M), the fluorescence sensitivity may be so low that the weak fluorescence signals might not be detectable, leading to false negative estimations. An experienced user could fix that limitation by changing the imaging settings. However, some users might not have the necessary experience.

SUMMARY

There may be a desire for an improved concept for operating a surgical imaging system.

This desire is addressed by the subject-matter of the independent claims.

Various examples of the present disclosure are based on the finding, that it is, in many cases, feasible to determine, for a given surgical procedure, a set of settings that is particularly suitable for that scenario. For example, if fluorescence imaging is being used, this set of settings may be chosen such, that a small working distance is combined with a low magnification, to increase the amount of fluorescence emissions being measured by the optical imaging sensor of the imaging device. In other scenarios, other sets of settings may be suitable. These settings may be determined, and the user of the surgical imaging system, e.g., the surgeon, may be provided with information on which settings are to be changed to arrive at the settings that are deemed to be suitable for the surgical procedure. The proposed concept thus provides a concept for helping the surgeon to improve the use of the imaging device.

Various examples of the present disclosure relate to a system for an imaging device of a surgical imaging system. The system comprises one or more processors and one or more storage devices. The system is configured to determine a first set of settings being suitable for using the imaging device in a surgical procedure. The system is configured to determine a second set of settings currently being used. The system is configured to provide a signal indicating a difference between the first and second set of settings. The signal comprises information on at least one setting to adjust to obtain the first set of settings. By determining the first set of settings that are suitable for using the imaging device in a (given) surgical procedure, settings are established that can be used to improve the use of the imaging device. The second set of settings, on the other hand, represents the currently used settings. The signal is provided to help the surgeon change the settings in order to attain suitable settings for performing the surgical procedure. This leaves control over the respective settings with the surgeon, to give the surgeon ultimate control and responsibility over the settings being used.

In general, visual clues may be used to assist the user or surgeon in attaining the set of suitable settings. For example, the signal indicating the difference between the first and second set of settings may be a display signal. The display signal may comprise a visual representation of the information on the at least one setting to adjust to obtain the first set of settings, for example. Visual settings are often useful, as multiple pieces of information can be conveyed at the same time, over a longer period of time (e.g., compared to audio signals).

For example, the surgical imaging system may comprise a digital imaging device, where a digital view of the surgical site is provided based on imaging sensor data obtained from an optical imaging sensor of the imaging device. The visual representation may be included in the digital view, e.g., superimposed over a portion of the digital view, or to the side from the digital view. For example, the system may be configured to provide a digital view on a surgical site as part of the display signal. The digital view being based on imaging sensor data of an optical imaging sensor of the imaging device. The system may be configured to provide the visual representation of the information on the at least one setting to adjust to obtain the first set of settings overlaid over the digital view (or off to the side). This way, the information may be available to the surgeon at a glance at any time.

While the surgeon may try to limit the (digital) field of view to the surgical site, in many cases, the shape of the surgical site does not correspond to the shape of the field of view, so that some portions of the field of view are of less interest to the surgeon. These portions of the field of view may be used to display the information on the at least one setting to adjust. For example, the system may be configured to determine an area of interest for the surgical procedure within the imaging sensor data. The system may be configured to generate the display signal such, that the information on the at least one setting to adjust is shown outside the area of interest.

There are various ways to display the information on the at least one setting to adjust. In experiments, visual elements such as bar gauges and round gouges have been found to intuitively convey the information on the at least one setting to adjust. Accordingly, the system may be configured to provide the information on the at least one setting to adjust using one or more visual round gauges or bar gauges.

However, the proposed concept is not limited to digital imaging devices. For example, the signal indicating the difference between the first and second set of settings may be a signal for controlling one or more indicator lights of the surgical imaging system. The system may be configured to control the one or more indicator lights to provide the information on the at least one setting to adjust to obtain the first set of settings. This approach can be used with both digital and purely optical imaging devices.

Moreover, the provision of the information on the at least one setting to adjust might not be limited to visual representations. For example, the signal indicating the difference between the first and second set of settings may be an audio signal. As audible information, the information on the at least one setting to adjust to obtain the first set of settings may be perceived by the surgeon without taking the eyes off the surgical site.

As outlined above, the system is configured to provide suitable settings (i.e., the first set of settings) for a given surgical procedure. However, which settings are suitable may depend on the type and/or the progress of the surgical procedure. For example, if fluorescence imaging is used, a low working distance may be beneficial, which may be impractical in other scenarios, e.g., when multiple surgical instruments are required and the objective of the imaging device might hinder the operation of these instruments. For example, the system may be configured to determine the first set of settings based on a type of the surgical procedure. Moreover, the first set of settings may be updated based on the progress of the surgical procedure. The system may be configured to track the progress of the surgical procedure, and to determine the first set of settings based on the progress of the surgical procedure.

Many surgical procedures are routine procedures that proceed according to a sequence of steps. For each of these steps, suitable settings may be stored in the system, which may then be used to determine the first set of settings. For example, the progress of the surgical procedure comprises a plurality of steps. The system may comprise information on settings being suitable during the respective steps of the surgical procedure.

In some examples, not the actual settings might be stored, but the respective "objectives" to be fulfilled. In this context, an objective refers to an aspect of optical performance that is to be prioritized over one or more other aspects of optical performance of the imaging device. For example, some surgical procedures or steps of surgical procedure may have the objective of "increasing the optical resolution", e.g., to identify tiny pieces of tissue, while other procedures or steps may have the objective of "increasing the measurement of fluorescence emissions", e.g., to obtain a detailed fluorescence image, or of "increasing the depth of field", e.g., to operate in deep wound tracts. For example, the system may be configured to select an objective for determining the first set of settings according to the progress of the surgical procedure, and to determine the first set of settings based on the objective. For example, the system may be configured to select between a first objective for increasing a spatial resolution of the imaging device and a second objective for increasing an optical depth of field of the imaging device. A third objective may be an objective for increasing the measurement of fluorescence emissions. In other words, the objective being selected may relate to a quality of a representation of fluorescence emissions in imaging sensor data of an optical imaging sensor of the imaging device, e.g., with respect to an intensity, resolution, or depth of field of the measured fluorescence emissions.

When objectives are used instead of, or in addition to, pre-defined settings, a sweeping process may be used to determine the first set of settings. In other words, the settings may be varied, and the settings that (best) attain the objective may be chosen. For example, the system may be configured to sweep values of one or more settings of the set of settings, and to evaluate the resulting optical performance in view of the objective, to determine the first set of settings.

For example, the imaging sensor data of the optical imaging sensor of the imaging device, or depth sensor data, may be used to determine the first set of settings, e.g., the imaging sensor data may be used to evaluate the resulting optical performance. For example, the system may be configured to determine the first set of settings based on the imaging sensor data of the optical imaging sensor of the imaging device and/or based on depth sensor data of a depth sensor of the surgical imaging system.

There are various settings that have an impact on the optical performance of the imaging device. For example, the first and second set of settings may comprise one or more of the group of a working distance of the imaging device, an illumination provided by an illumination system of the surgical imaging system, a zoom level of the imaging device, and an aperture of the imaging device.

In some cases, it may be desirable to subdivide the settings in two groups of settings—a first subset of settings that should (or even have to) be adjusted by the surgeon, and a second subset of settings that can be adjusted automatically. For example, while working distance and zoom level are often manually controlled by the surgeon, other settings such as the sensitivity of the optical imaging sensor and/or the aperture of the objective are rarely controlled manually, as controlling these aspects is often found to be too complex during surgical procedures. For example, each set of settings may comprise a first and a second subset of settings. The system may be configured to generate the signal indicating the difference between the first and second set of settings for the first subset of settings, and to automatically adjust the second subset of settings based on the first set of settings. For example, the first subset of settings may comprise at least one of a working distance of the imaging device and a zoom level of the imaging device. For example, the second subset of settings may comprise at least one of an aperture of the imaging device and a sensitivity of an optical sensor of the imaging device.

In many cases, surgical imaging system are used by surgeons over many hours, making them an integral tool for surgeons such as neurosurgeons or for surgeons performing ophthalmic procedures. In many cases, these surgeons develop personal preferences with respect to the use of the surgical imaging system. In some examples of the present disclosure, machine-learning may be used to reflect these personal preferences. For example, the system may be configured to adapt the first set of settings using a machine-learning model being trained to reflect a preference of a specific surgeon.

In general, during surgery, the surgeon concentrates on the task at hand. An abundance of information may, in some cases, make it harder for the surgeon to concentrate on surgery. Therefore, in some examples, the signal indicating the difference between the first and second set of settings might (only) be provided when the surgeon is found to be inactive, e.g., between steps of the surgical procedure. For example, the system may be configured to track an activity of a surgeon using imaging sensor data of an optical imaging sensor of the imaging device. The system may be configured to detect a period of inactivity of the surgeon, and to provide the signal indicating the difference between the first and second set of settings (only) when a period of inactivity of the surgeon is detected.

The proposed concept is applicable to various types of imaging devices and surgical imaging systems. For example, the imaging device may be microscope. Accordingly, the surgical imaging system may be a surgical microscope system. Alternatively, the imaging device may be an endoscope. Accordingly, the surgical imaging system may be a surgical endoscope system. Alternatively, the imaging device may be an exoscope. Accordingly, the surgical imaging system may be a surgical exoscope system.

Various examples of the present disclosure further provide a surgical imaging system comprising the imaging device and the system. For example, the present disclosure may provide at least one of a surgical microscope system comprising a microscope, a surgical endoscope system comprising an endoscope and a surgical exoscope system comprising an exoscope.

Various examples of the present disclosure relate to a (corresponding) method for a imaging device of a surgical imaging system. The method comprises determining a first set of settings being suitable for using the imaging device in a surgical procedure. The method comprises determining a second set of settings currently being used. The method comprises providing a signal indicating a difference between the first and second set of settings, the signal comprising information on at least one setting to adjust to obtain the first set of settings.

Various examples of the present disclosure relate to a (corresponding) computer program with a program code for performing the above method when the computer program is executed on a processor.

SHORT DESCRIPTION OF THE FIGURES

Some examples of apparatuses and/or methods will be described in the following by way of example only, and with reference to the accompanying figures, in which FIG. 1*a* shows a block diagram of an example of a system for a imaging device of a surgical imaging system;

FIG. 1*b* shows a schematic diagram of an example of a surgical imaging system;

DETAILED DESCRIPTION

Various examples will now be described more fully with reference to the accompanying drawings in which some examples are illustrated. In the figures, the thicknesses of lines, layers and/or regions may be exaggerated for clarity.

Figure 1A:
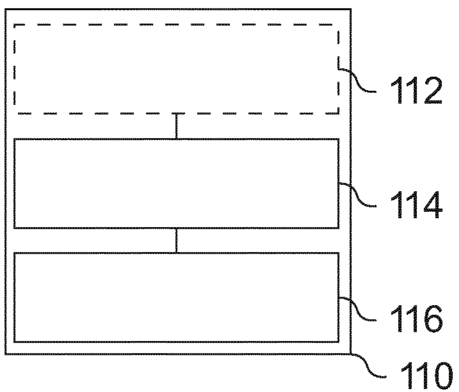

FIG. 1*a* shows a block diagram of an example of a system 110 for a imaging device 120 of a surgical imaging system 100. The system comprises one or more processors 114 and one or more storage devices 116. Optionally, the system further comprises one or more interfaces 112. The one or more processors 114 are coupled to the one or more storage devices 116 and to the optional one or more interfaces 112. In general, the functionality of the system is provided by the one or more processors, in conjunction with the one or more interfaces (for exchanging information, e.g., with an optical imaging sensor of a imaging device, a depth sensor of the surgical imaging system and/or with a display device of the surgical imaging system) and/or with the one or more storage devices (for storing and/or retrieving information).

The system is configured to determine a first set of settings being suitable for using the imaging device in a surgical procedure. The system is configured to determine a second set of settings currently being used. The system is configured to provide a signal indicating a difference between the first and second set of settings. The signal comprises information on at least one setting to adjust to obtain the first set of settings.

Figure 1B:
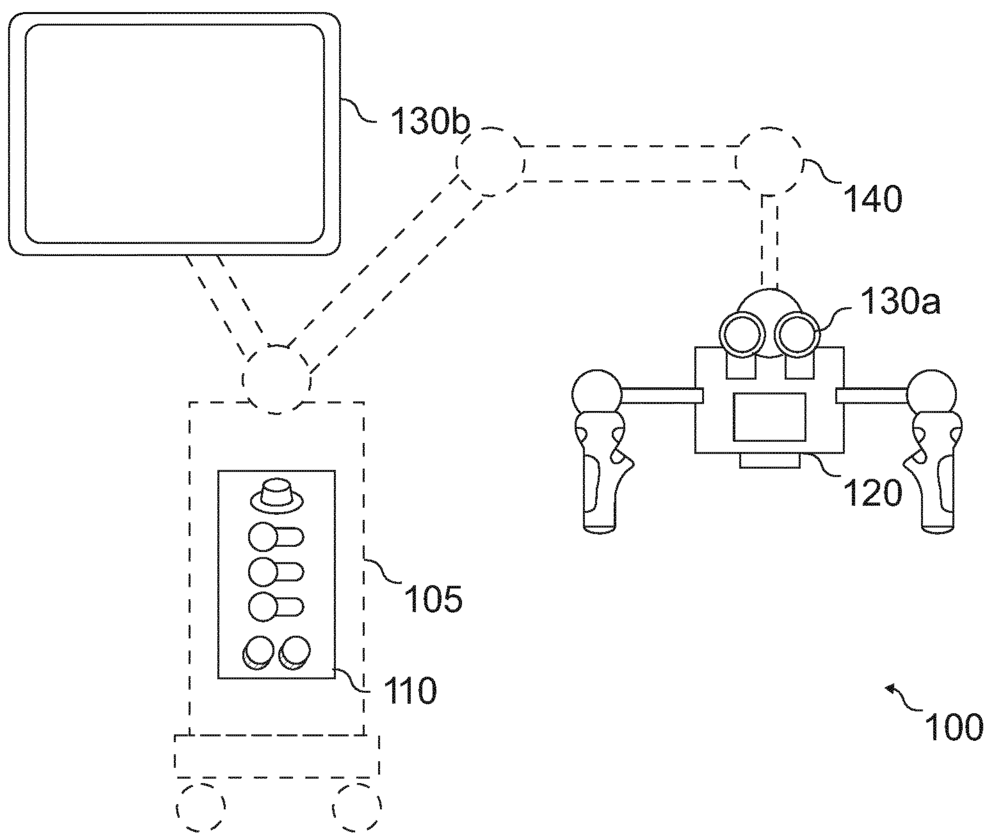

The proposed concept, and in particular the proposed system 110, is a system for a imaging device of a surgical imaging system. For example, the system 110 may be a computer system that is coupled with the imaging device 120 (as shown in FIG. 1*b*). The system 110 may provide processing capabilities and/or control capabilities that may be used to augment the functionality of the surgical imaging system, and in particular of the imaging device. For example, the proposed system may assist a user of the imaging device, e.g., a surgeon, in adjusting the settings of the imaging device and/or of the surgical imaging system to settings that are suitable in view of the surgical procedure being performed.

The proposed system is used in conjunction with the imaging device 120. The proposed concept is suitable for different types of imaging devices. For example, the imaging device may be a microscope. In general, a microscope is an optical instrument that is suitable for examining objects that are too small to be examined by the human eye (alone). For example, a microscope may provide an optical magnification of a sample. In modern microscopes, the optical magnification is often provided for a camera or an imaging sensor, such as the optical imaging sensor of the microscope 120 that is shown in FIG. 1*b*. The microscope 120 may further comprise one or more optical magnification components that are used to magnify a view on the sample, such as an objective (i.e., lens).

Alternatively, the imaging device 120 may be an endoscope. A (surgical) endoscope is a (surgical) instrument that is suitable for inspecting a cavity. An endoscope generally comprises a housing with a lens, an optical imaging sensor and an illumination modality (with the illumination being provided by an LED that is included in the housing or via a light guide). The housing of the endoscope is connected, usually via wires, to a control unit, such as the system 110. As outlined above, an endoscope may be used for inspecting cavities. These cavities may be accessible via surgical incisions, or via openings of the body, such as the mouth or the anus of the body.

As yet another alternative, the imaging device 120 may be an exoscope (also sometimes called an extracorporeal telescope). Exoscopes are camera-based imaging systems, and in particular camera-based 3D imaging systems, that are suitable for providing images of surgical sites with high magnification and a large depth of field. Compared to microscopes, which may be used via oculars, exoscopes are only used via display modalities, such as a monitor or a head-mounted display.

There are a variety of different types of imaging devices, and in particular microscopes. If the microscope is used in the medical or biological fields, the object being viewed through the microscope may be a sample of organic tissue, e.g., arranged within a petri dish or present in a part of a body of a patient. In the present case, the imaging device is a imaging device of a surgical imaging system, i.e., a imaging device that is to be used during a surgical procedure, such as a neurosurgical procedure or an ophthalmic procedure. Such a system is shown in FIG. 1*b*, for example. Accordingly, an object being viewed through the imaging device, and shown in the image data, may be a sample of organic tissue of a patient, and may be in particular be a surgical site that the surgeon operates on during the surgical procedure.

The above system 110 is suitable for use with the surgical imaging system comprising the imaging device 120, e.g., as part of the surgical imaging system 100. FIG. 1*b* shows a schematic diagram of an example of the surgical imaging system 100, and in particular a surgical microscope system 100, comprising the system 110 and the imaging device 120. The imaging device system shown in FIG. 1*b* is a surgical microscope system. However, the system 110 may be used with other imaging device systems or optical systems as well, in particular surgical imaging systems comprising an endoscope or exoscope. The surgical microscope system 100 shown in FIG. 1*b* comprises a number of optional components, such as a base unit 105 (comprising the system 110) with a (rolling) stand, ocular displays 130*a* that are arranged at the microscope 120, a display 130*b* that is arranged at the base unit and a (robotic or manual) arm 140 which holds the microscope 120 in place, and which is coupled to the base unit 105 and to the microscope 120. In the context of this application, the term "(surgical) microscope system" is used, in order to cover the portions of the system that are not part of the actual microscope (which comprises the optical components), but which are used in conjunction with the microscope, such as the display or an illumination system.

The proposed concept focuses on tasks being performed by the system 110. In particular, the proposed concept is based on determining settings that are suitable for using the imaging device in a given surgical procedure, comparing these settings with settings currently being used, and guiding the user (i.e., surgeon) of the imaging device on how to change the settings to obtain improved settings. In other words, the proposed concept may be used to guide a user of the imaging device with respect to the settings of the imaging device (or, more generally, of the surgical imaging system), so that the settings eventually chosen by the user are suitable for the surgical procedure. In particular, the settings being referred to in the present disclosure are settings that have an impact on the optical performance of the imaging device. In other words, the first and second set of settings may comprise, or correspond to, settings that have an impact on the optical performance of the imaging device. For example, the first and second set of settings may comprise one or more of the group of a working distance of the imaging device, an illumination provided by an illumination system of the surgical imaging system (e.g., the illumination intensity), a zoom level of the imaging device (i.e., a magnification provided by an optical zoom of the objective of the imaging device), and an aperture of the imaging device (i.e., the aperture being selected for the objective of the imaging device). As is evident, while the first set of settings is suitable for using the imaging device in the surgical procedure, the respective settings may relate to other components of the surgical imaging system as well, such as the working distance (that is controlled by or via the arm of the surgical imaging system) and the illumination (that is provided by the illumination system).

The system is configured to determine the first set of settings, with the first set of settings being suitable for using the imaging device in a surgical procedure. In this context, the term "suitable for the imaging device in the surgical procedure" indicates that the first set of settings is chosen such, that the surgeon is able to perform the surgical procedure using the imaging device, without impairment due to incorrectly selected settings. In some examples, the first set of settings may be settings that are optimal with respect to the surgical procedure, or with respect to a step of the surgical procedure. More generally, however, the first set of settings may be settings that are more suited during the surgical procedure than at least one different set of settings, e.g., more suited than the second set of settings. While the present disclosure relates to first and second "sets of settings" that are potentially suitable for using the imaging device in the surgical procedure, it is the values chosen for the respective settings of the set of settings that are suitable for using the imaging device in the surgical procedure.

The first set of settings are suitable for using the imaging device in a surgical procedure, e.g., in a given or specific surgical procedure, or in a step of the given or specific surgical procedure. Therefore, the first set of settings may be dependent on the surgical procedure being performed. In other words, the first set of settings may be specific for the surgical procedure being performed. For example, different types of surgical procedures may yield different first sets of settings. Accordingly, the system may be configured to determine the first set of settings based on the type of the surgical procedure. For example, the type of the surgical procedure may be input by a user of the surgical imaging system at the start of the surgical procedure, it may be derived from a pre-operative plan being input or stored into the system/surgical imaging system, or the system may be configured to determine the type of the surgical procedure using object detection based on imaging sensor data of an optical imaging sensor of the imaging device.

For example, depending on the type of the surgical performance being performed, different objectives may be relevant. For example, for some surgical procedures, the performance of fluorescence imaging may be particularly relevant, so the objective may be to increase the measurement of fluorescence emissions. In other words, the objective being selected may relate to a quality of a representation of fluorescence emissions in the imaging sensor data of the optical imaging sensor of the imaging device. Other objectives may be to increase the spatial resolution (i.e., to increase the level of detail being measured by the optical imaging sensor of the imaging device), or to increase the depth of field (i.e., to accommodate surgical sites with a non-flat depth profile), e.g., with respect to the fluorescence emissions being measured. In particular, the objective being selected may relate to the quality of the representation of the fluorescence emissions with respect to at least one of an intensity (i.e., amplitude of the measured fluorescence emissions in the imaging sensor data), resolution and depth of field of the measured fluorescence emissions. In general, properties such as the resolution and the depth of field may equally apply to fluorescence and reflectance imaging. According to the objective, the first set of settings may be chosen. For example, to increase the measurement of fluorescence emissions, the working distance may be decreased and the zoom level may be decreased, thereby retaining the field of view, while increasing the amount of fluorescence emissions being measured by the optical imaging sensor. To increase the spatial resolution (e.g., the optical resolution of the imaging device, not the resolution in terms of pixels of the optical imaging sensor), the light intensity may be increased, and/or the working distance may be decreased and the zoom level may be decreased, thereby retaining the field of view, while increasing the amount of light being measured by the optical imaging sensor. When the amount of light is increased, the aperture of the objective of the imaging device may be decreased and/or the sensitivity of the optical imaging sensor may be decrease. This may both increase the spatial resolution, as a imaging device objective that does not operate at its largest aperture tends to show improved optical performance with respect to details being shown, and as a lower sensor sensitivity results in reduced noise, which may also translate into an increase spatial resolution. To increase the depth of field, the aperture of the objective may be decreased, which may necessitate lowering the working distance and zoom level, increasing the illumination intensity, and/or increasing the sensitivity of the optical imaging sensor, to account for the decreased amount of light passing through the decreased aperture of the objective of the imaging device. As is evident, each of the objectives may have an impact on one or more setting of the first set of settings. The system may be configured to select an objective for determining the first set of settings according to the surgical procedure being performed (e.g., according to the type of the surgical procedure), and to determine the first set of settings based on the objective.

When the first set of settings is determined based on an objective, some amount of trial and error may be used to determine the settings. In other words, the settings may be varied (e.g., by sweeping them in a methodological fashion), e.g., starting from a pre-defined set of initial settings that is known for the objective, until the first set of settings is established that is suitable (e.g., optimal or better than others) for using the imaging device in the surgical procedure. For example, the system may be configured to sweep values of one or more settings of the set of settings, and to evaluate the resulting optical performance in view of the objective, to determine the first set of settings. In this context, sweeping values of the one or more settings indicates that the respective values are varied according to a pre-defined scheme. For example, starting from the initial set of settings, a value of a setting may be increased or decreased by a pre-defined (small) value, and the resulting optical performance may be measured (using the optical imaging sensor). If the optical performance increases, the adjustment may be repeated (e.g., the value may be further increased or decreased) until the optical performance decreases. Then, the sweeping procedure may continue with the next setting. Alternatively, the value of multiple settings may be changed at the same time, followed by the evaluation of the optical performance. In some examples, a pre-defined plurality of different values and/or combination of values may be tried and evaluated. A suitable set of settings (e.g., the set of settings that results in the highest optical performance, or, more generally, a set of settings that results in a higher optical performance than other sets of settings) may be selected based on the evaluation. In general, the sweeping procedure may be limited, i.e., the values being selected during sweeping may be limited, e.g., based on the type of the surgical procedure. For example, some types of surgical procedures may have limits regarding a minimal working distance (to allow for the utilization of surgical instruments) or regarding a maximal illumination intensity (to avoid damaging the tissue during the surgical procedure). For example, some settings might not be suitable for sweeping, such as the working distance, as such a sweep may require a robotic arm and/or might interfere with the surgical procedure. For example, the sweeping procedure may be performed during a period of inactivity of the surgeon, e.g., before the start of the surgical procedure or between steps of the surgical procedure.

To determine the optical performance resulting from the settings, e.g., during the sweeping procedure, the imaging sensor data of the optical imaging sensor may be used. For example, the system may be configured to calculate a measure for the spatial resolution, a measure for the depth of field, and/or a measure for the intensity of the measured fluorescence emission based on the optical imaging sensor data, e.g., by evaluating the sharpness of edges visible in the imaging sensor data, with sharper edges at the focusing distance indicating a higher spatial resolution, and with sharp edges being visible at various (surgically relevant) depths of the surgical tract indicating a suitable depth of field, or by evaluating the intensity of light in a fluorescence emission wavelength band.

In some examples, the imaging sensor data, and/or other sensor data, as depth sensor data, may also be used to determine the objective, and thereby the first set of settings. For example, the system may be configured to determine the first set of settings based on the imaging sensor data of the optical imaging sensor of the imaging device and/or based on the depth sensor data of a depth sensor of the surgical imaging system. In particular, the system may be configured to select the objective based on the imaging sensor data of the optical imaging sensor of the imaging device and/or based on the depth sensor data. For example, the system may be configured to use object detection on the imaging sensor data to identify the surgical site, e.g., the extent of the surgical site. The system may also be configured to use object detection to identify a type of the surgical site, and therefore also the type of the surgical procedure. For example, depending on the detected type of the surgical site and/or of the detected type of the surgical procedure, a suitable objective may be chosen. For example, depending on the type of the surgical procedure, the objective of increasing the spatial resolution, the objective of increasing the optical depth of field, or the objective of increasing the intensity of the measured fluorescence emissions may be selected. Moreover, the depth sensor data may be used to determine whether the surgical procedure is performed on a surgical site that would benefit from an increased depth of field (e.g., based on the depth profile of the surgical site). For example, the system may be configured to select between a first objective for increasing a spatial resolution of the imaging device and a second objective for increasing an optical depth of field of the imaging device.

So far, the type of the surgical procedure has been used to determine the first set of settings, e.g., via the objective being selected. However, many surgical procedures comprise multiple tasks or steps, with different objectives and sets of settings being suitable for different tasks, or at different steps, of the surgical procedure. Accordingly, the system may be configured to track a progress of the surgical procedure, and to determine the first set of settings based on the progress of the surgical procedure. For example, the progress of the surgical procedure may comprise a plurality of steps, and the system may be configured to determine the current step of the surgical procedure. To determine the current step of the surgical procedure, the system may be configured to use the aforementioned object detection (e.g., in combination with a pre-operative plan). Alternatively, the system may be configured to obtain an input from a user of the surgical imaging system (e.g., via a touchscreen or via voice recognition), with the input indicating the current step, and therefore the progress, of the surgical procedure.

Based on the progress of the surgical procedure, e.g., based on the current step, the first set of settings may be determined. For example, the system, e.g. the one or more storage devices 116, may comprise information on settings being suitable during the respective steps of the surgical procedure. The system may be configured to obtain the first set of settings based on the information on the settings being suitable during the respective steps of the surgical procedure and based on the current step of the optical procedure. In some examples, the information on the settings being suitable during the respective steps of the surgical procedure may comprise the actual values of the settings. Alternatively, the information on the settings being suitable during the respective steps of the surgical procedure may comprise information on an objective to use during the respective steps of the surgical procedure. The information on the settings being suitable during the respective steps of the surgical procedure may further comprise, for the respective objectives, corresponding initial starting values for the sweeping procedure. For example, the system may be configured to select the objective for determining the first set of settings according to the progress of the surgical procedure (e.g., based on the information on the settings being suitable during the respective steps of the surgical procedure), and to determine the first set of settings based on the selected objective.

The proposed concept is based on comparing the first set of settings, which is known to be suitable for using the imaging device in the surgical procedure (e.g., at the current step of the surgical procedure), with the second set of settings, which are the settings that are currently being used. For example, the second set of settings may be settings of the imaging device and/or of the surgical imaging system. The system may be configured to read out the second set of settings from one or more sensors or actors of the imaging device and/or imaging device system (e.g., via the interface 112).

Based on the different between the first and second set of settings, a signal is provided that comprises information on at least one setting to adjust to obtain the first set of settings. In other words, the system may be configured to provide information on how to change the currently used (second) set of settings to obtain settings that are more suitable for using the imaging device in the surgical procedure. For example, system may be configured to provide information how to improve the currently used (second) set of settings with respect to the surgical procedure, by providing the information on how to change the currently used (second) set of settings to obtain suitable settings. However, this might not always be necessary. For example, if the difference between the first set of settings and the second of settings is low, e.g., smaller than a threshold, the system may be configured to forego (e.g., refrain from) providing the signal indicating the difference between the first and second set of settings.

The signal indicating the difference between the first and second set of settings comprises information on at least one setting to adjust to obtain the first set of settings. This information can be conveyed using different types of signals. Therefore, different representations of the information on at least one setting to adjust to obtain the first set of settings may be used.

For example, the information on at least one setting to adjust to obtain the first set of settings may be provided visually, e.g., via a display of the surgical imaging system, or via dedicated indicator lights of the surgical imaging system. For example, the signal indicating the difference between the first and second set of settings may be a display signal, with the display signal comprising a visual representation of the information on the at least one setting to adjust to obtain the first set of settings. In other words, the display signal may be used to drive a display of the surgical imaging system, so that the information on the at least one setting to adjust to obtain the first set of settings is shown on the display.

Figure 3:
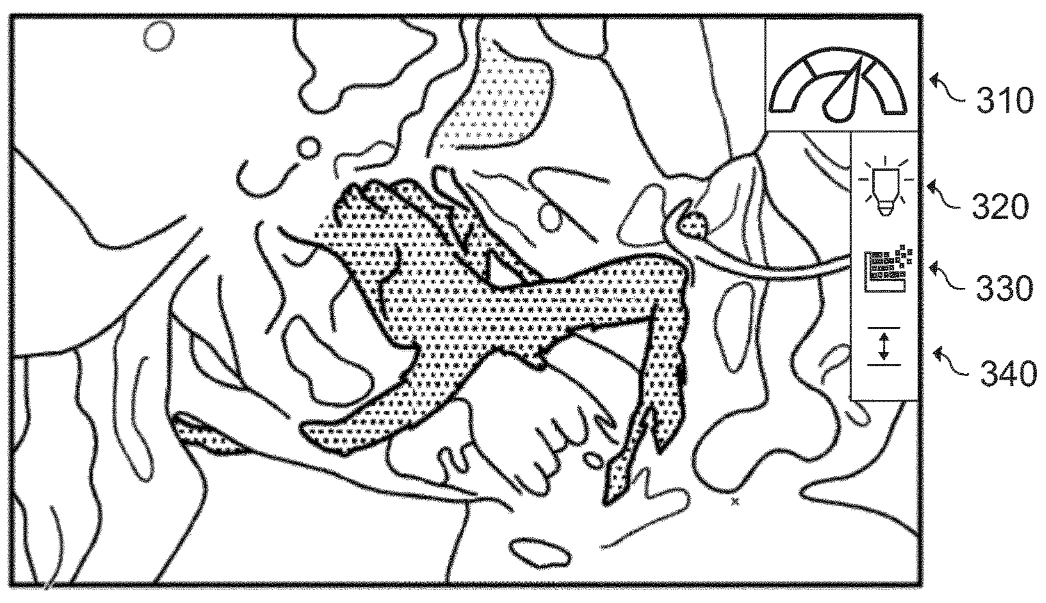
FIG. 3 shows a schematic diagram of an example of an overlay that is superimposed over a digital view of a surgical site.

In many surgical imaging system, the view on the surgical site is provided digitally. Such a digital view may be generated based on the imaging sensor data of the optical imaging sensor of the imaging device. In other words, the system may be configured to provide a digital view on a surgical site as part of the display signal, with the digital view being based on the imaging sensor data of the optical imaging sensor of the imaging device. This digital view may provide a view on the surgical site that is enhanced over the purely optical view, e.g., by adding a fluorescence imaging overlay in pseudocolor, by overlaying information derived from additional sensors, or by providing an overlay that is based on object detection and image segmentation. With respect to the proposed concept, the information on the at least one setting to adjust to obtain the first set of settings may be added on top of the digital view, or side by side with the digital view, and output with the display signal. In other words, the system may be configured to provide the visual representation of the information on the at least one setting to adjust to obtain the first set of settings overlaid (i.e., superimposed) over the digital view or side by side with the digital view. In FIG. 3, an example is shown where four indicators 310-340 are shown overlaid over the digital view, at the right side of the digital view.

The visual representation of the information on the at least one setting to adjust may take many forms. In experiments, a colored pictogram representation was found to be effective in conveying the information. For example, the colors of the traffic light may be used to convey whether the respective settings are suitable, with red indicating unsuitable settings, yellow indicating suitable, but less than optimal settings, and green indicating optical settings. The colors may indicate the at least one setting to adjust. For example, as shown in FIG. 3 for indicators 320-340, for each setting (e.g., each setting found to be unsuitable or less than optimal), a colored pictogram may be shown. In this case, the presence of the pictogram, and the colors may indicate the at least one setting to adjust. Beside the pictogram, an arrow may be shown, indicating in which direction the setting is to be adjusted. As also shown in FIG. 3, gauges, such as round gauges or bar gauges may also be used to convey the information on the at least one setting, e.g. by indicating, using color, which portion of the range of values of a particular setting is deemed to be suitable. Accordingly, the system may be configured to provide the information on the at least one setting to adjust using one or more visual round gauges or bar gauges. Apart from pictograms or gauges, a textual representation may be used to convey the information on the at least one setting.

As is evident from FIG. 3, the visual representation of the information on the at least one setting may be included such, that the digital view remains mostly unobstructed, e.g., by placing the visual representation off to the side. In some examples, the afore-mentioned object detection of the surgical site may be used to place the visual representation relative to the digital view. For example, the system may be configured to determine an area of interest for the surgical procedure (e.g., the surgical site or a portion of the surgical site the surgeon is currently operating on) within the imaging sensor data, e.g., using object detection. The system may be configured to generate the display signal such, that the information on the at least one setting to adjust is shown outside the area of interest. For example, the system may be configured to place the visual representation at an edge of the digital view that is furthest away from the area of interest.

The display signal may be provided to a display 130*a*; 130*b* of the imaging device system 100. In other words, the system may be configured to provide the display signal comprising the information on at least one setting to adjust to obtain the first set of settings to a display 130*a*; 130*b* of the imaging device system. For example, the display signal may be a signal for driving (e.g., controlling) the display 130*a*; 130*b*. For example, the display signal may comprise video data and/or control instructions for driving the display. For example, the display signal may be provided via one of the one or more interfaces 112 of the system. Accordingly, the system 110 may comprise a video interface 112 that is suitable for providing the video signal to the display of the touch screen.

Apart from a display, dedicated lights may be used to visually convey the information on the at least one setting. For example, the signal indicating the difference between the first and second set of settings may be a signal for controlling one or more indicator lights of the surgical imaging system. For example, each of the indicator lights may represent a setting, and a color selected for the light may convey whether the setting is suitable or a direction in which a value of the setting is to be changed to attain suitability. The system may be configured to control the one or more indicator lights to provide the information on the at least one setting to adjust to obtain the first set of settings. For example, the system may be configured to control a color or an activation of the one or more indicator lights to convey the information on the at least one setting. Alternatively, the signal indicating the difference between the first and second set of settings is an audio signal. The system may be configured to provide the information on the at least one setting via text-to-speech within the audio signal.

For example, the signal indicating the difference between the first and second set of settings may be provided to the one or more indicator lights or to a loudspeaker, respectively, e.g., to a controller for controlling the one or more indicator lights or to an audio controller. For example, the signal indicating the difference between the first and second set of settings may be provided via the interface 112.

In the proposed concept, instead of directly manipulating the settings, the basic idea is to guide the surgeon to make the changes themselves, which improves the predictability of the system for the respective surgeon. However, there are some settings that take increased effort to control manually, e.g., as the effect is hard to estimate for the surgeon. For example, while the surgeon may manually adjust the aperture of the objective, the effects of such a manual adjustment are hard to oversee, as they depend on the depth profile of the surgical site, on the working distance and on the zoom level. Therefore, some of the settings may be adjusted automatically, while other settings remain under the direct control of the surgeon.

For example, each set of settings may comprise a first and a second subset of settings. The system may be configured to generate the signal indicating the difference between the first and second set of settings for the first subset of settings, and to automatically adjust the second subset of settings based on the first set of settings. In other words, the first subset of settings may be changed manually by the surgeon, whereas the second subset of settings may be changed automatically. For example, the first subset of settings may comprise at least one of the working distance of the imaging device and the zoom level of the imaging device. The second subset of settings may comprise at least one of the aperture of the imaging device (i.e., the aperture settings of the objective of the imaging device) and the sensitivity of the optical sensor of the imaging device. Other settings, such as the illumination intensity, may be in either subset.

As outlined above, it may be desirable to avoid distracting the surgeon with the signal indicating the difference between the first and second set of settings. This may be done by keeping the digital view mostly unobstructed by the visual representation. In some examples, additionally or alternatively, the signal indicating the difference between the first and second set of settings might only be provided while the surgeon is not concentrated on the surgery, e.g., between steps of the surgical procedure, or while an assistant performs a task. The system may be configured to detect such periods of inactivity by the (main) surgeon and provide the signal indicating the difference between the first and second set of settings only when such a period of inactivity is detected. Accordingly, the system may be configured to track an activity of a surgeon using the imaging sensor data of an optical imaging sensor of the imaging device to detect a period of inactivity of the surgeon. For example, the system may be configured to use object detection to detect surgical instruments being used on the surgical site. If the instrument being used by the surgeon is seen to be withdrawn from the surgical site, a period of inactivity may be detected. Moreover, the object detection may be used to detect when the progress of the surgical procedure advances to a subsequent step, with a period of inactivity being detected between steps. For example, the aforementioned tracking of the progress of the surgical procedure may be used to detect periods of inactivity. The system may be configured provide the signal indicating the difference between the first and second set of settings when (e.g., while) a period of inactivity of the surgeon is detected, e.g., only during periods of inactivity.

Surgeons often use the respective surgical imaging systems over long stretches of time, on many days a week. They often develop habits and preferences and adjust the settings to their liking. Therefore, the definition of what a suitable or optimal set of setting is can be surgeon-specific. In some examples of the present disclosure, machine-learning may be used to learn the preferences of the individual surgeons and use the learned preferences to tailor the first set of preferences to the surgeon. Accordingly, the system may be configured to adapt the first set of settings using a machine-learning model being trained to reflect a preference of a specific surgeon. In other words, the machine-learning model may be used as filter that is used to tailor the first set of settings to the preferences of the surgeon. For example, the machine-learning model may be trained, e.g., using supervised learning, to provide an adapted first set of settings based on the first set of settings that is non-surgeon-specific. This may be done by recording a plurality of samples of first sets of settings (that are nonsurgeon-specific) and a plurality of corresponding sets of settings that are chosen by the surgeon. The plurality of samples of first sets of settings, or rather a subset of them, may be input as training input samples, and the corresponding settings chosen by the surgeon may be used as desired output of the machine-learning model. Based on the training input samples and the corresponding desired output, the machine-learning model may be trained using supervised learning. Some of the training input samples and corresponding desired outputs may be omitted from the training and be used to verify that the machine-learning model is suitable for adapting the first set of settings to the preferences of the surgeon, e.g., by ascertaining that a delta between the adapted first set of settings and the corresponding desired output is smaller than a threshold. If the delta is too large, the training may be continued until the delta is small enough.

In some examples, the system is configured to track the progress of the surgical procedure and/or to perform object detection, e.g. to detect surgical instruments, to determine at which step the progress of the surgical procedure, or to determine the extent of the surgical site. For example, respective machine-learning models may be used to perform these tasks. For example, a machine-learning model that is trained to perform object detection (of surgical instruments, of different types of surgical sites, of different types of surgical procedures etc.) may be used to perform the respective task. For example, imaging sensor data representing the respective surgical instruments, types if surgical sites or types of surgical procedures may be used to training input samples, and a suitable desired output, such as the type and location of the object, the type and extent of the surgical site, the type of the surgical procedure etc., may be used as desired output. Using this data, the respective machine-learning model may be trained using supervised learning. For example, a separate machine-learning model may be used for each task.

In the present disclosure, fluorescence imaging is taken as example that benefits from the proposed concept. Some surgical imaging system provide the fluorescence imaging functionality, in which light is emitted towards the surgical site in a first wavelength band (also called the fluorescence excitation wavelength band). If a fluorescent dye is used in the surgical site, the emitted light excites the dye, and light is emitted in a second wavelength band (also called the fluorescence emission wavelength band). This light can be recorded by a camera sensor, such as the optical imaging sensor, and displayed on a display of the surgical imaging device, e.g. on a display of an ocular of the surgical imaging device. Compared with reflectance imaging, light that is emitted by the fluorescent dye has a low illumination intensity, so the settings may be tuned to ascertain that enough light can be measured by the optical imaging sensor. In some examples, different optical imaging sensors are used for fluorescence imaging and reflectance imaging. In some examples, wavelength bands are recorded separately by one or more optical imaging sensors (e.g., for the purposes of multi-spectral images), and one or more of the wavelength bands may be used for fluorescence imaging, e.g. by blocking light from the emission spectrum of the illumination system of the surgical imaging system that intersects with the fluorescence emission wavelength band.

In the proposed concept, the optical imaging sensor of the imaging device may be employed by the system to generate imaging sensor data of the surgical site, which the system may in turn evaluate to determine the first set of settings. Accordingly, the optical imaging sensor is configured to generate the imaging sensor data. For example, the optical imaging sensor of the imaging device 120 may comprise or be an APS (Active Pixel Sensor)—or a CCD (Charge-Coupled-Device)-based imaging sensor. For example, in APS-based imaging sensors, light is recorded at each pixel using a photo-detector and an active amplifier of the pixel. APS-based imaging sensors are often based on CMOS (Complementary Metal-Oxide-Semiconductor) or S-CMOS (Scientific CMOS) technology. In CCD-based imaging sensors, incoming photons are converted into electron charges at a semiconductor-oxide interface, which are subsequently moved between capacitive bins in the imaging sensors by a circuitry of the imaging sensors to perform the imaging. The system 110 may be configured to obtain (i.e., receive or read out) the imaging sensor data from the optical imaging sensor. The imaging sensor data may be obtained by receiving the imaging sensor data from the optical imaging sensor (e.g., via the interface 112), by reading the imaging sensor data out from a memory of the optical imaging sensor (e.g., via the interface 112), or by reading the imaging sensor data from a storage device 116 of the system 110, e.g., after the imaging sensor data has been written to the storage device 116 by the optical imaging sensor or by another system or processor.

The one or more interfaces 112 of the system 110 may correspond to one or more inputs and/or outputs for receiving and/or transmitting information, which may be in digital (bit) values according to a specified code, within a module, between modules or between modules of different entities. For example, the one or more interfaces 112 may comprise interface circuitry configured to receive and/or transmit information. The one or more processors 114 of the system 110 may be implemented using one or more processing units, one or more processing devices, any means for processing, such as a processor, a computer or a programmable hardware component being operable with accordingly adapted software. In other words, the described function of the one or more processors 114 may as well be implemented in software, which is then executed on one or more programmable hardware components. Such hardware components may comprise a general-purpose processor, a Digital Signal Processor (DSP), a micro-controller, etc. The one or more storage devices 116 of the system 110 may comprise at least one element of the group of a computer readable storage medium, such as a magnetic or optical storage medium, e.g., a hard disk drive, a flash memory, Floppy-Disk, Random Access Memory (RAM), Programmable Read Only Memory (PROM), Erasable Programmable Read Only Memory (EPROM), an Electronically Erasable Programmable Read Only Memory (EEPROM), or a network storage.

More details and aspects of the system and surgical imaging system are mentioned in connection with the proposed concept or one or more examples described above or below (e.g. FIG. 2 or 3). The system and surgical imaging system may comprise one or more additional optional features corresponding to one or more aspects of the proposed concept or one or more examples described above or below.

Figure 2:
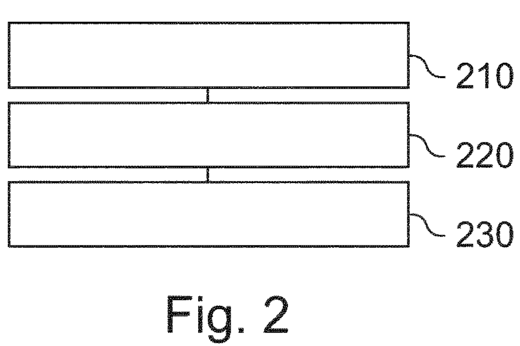
FIG. 2 shows a flow chart of an example of a method for a imaging device of a surgical imaging system.

FIG. 2 shows a flow chart of an example of a corresponding method for a imaging device of a surgical imaging system, e.g., for the imaging device 120 of the surgical imaging system 100 of FIGS. 1*a* and 1*b*. For example, the method may be performed by the surgical imaging system 100 of FIGS. 1*a* and/or 1*b*, and in particular by the system 110 of FIGS. 1*a* and/or 1*b*. The method comprises determining 210 a first set of settings being suitable for using the imaging device in a surgical procedure. The method comprises determining 220 a second set of settings currently being used. The method comprises providing 230 a signal indicating a difference between the first and second set of settings, the signal comprising information on at least one setting to adjust to obtain the first set of settings.

As indicated above, features described in connection with the system 110 and/or the surgical imaging system 100 of FIG. 1*b* may be likewise applied to the method of FIG. 2.

More details and aspects of the method are mentioned in connection with the proposed concept or one or more examples described above or below (e.g. FIGS. 1*a* to 1*b*, 3). The method may comprise one or more additional optional features corresponding to one or more aspects of the proposed concept or one or more examples described above or below.

Various examples of the present disclosure relates to an assistant for improving (e.g., optimizing) the use of a imaging device, such as a microscope, i.e., a microscope use improvement or optimization assistant.

In the proposed concept, the imaging device may inform the user about the suitability of the imaging conditions (e.g., about how suitable the chosen settings are compared with "optimal" or improved settings). Moreover, the imaging device may propose corrective actions or suitable (e.g., optimal) parameter values. Furthermore, the imaging device may also implement the proposed changes when physically possible (e.g., working distance may be adjusted with a robotic arm in case of a microscope or exoscope). For example, one or more of an illumination intensity, a working distance, a magnification, and an iris (i.e., aperture) may be adjusted.

In the following, an example is given with respect to fluorescence (FL) imaging. When the working distance of the imaging device is increased, the imaging device usually becomes less sensitive. This is often combined with a higher magnification (to limit the field of view to the surgical site), which may further decrease the optical quality. Moreover, FL sensitivity often decreases too with increasing the working distance. However, some surgeons may not be aware that such a decrease occurs, and may not know which parameters to align to increase the image quality. In the proposed concept, the imaging device informs the user about the imaging conditions, and if the imaging conditions are not good (e.g., not suitable for the surgical procedure), the imaging device may warn the user and propose proper settings or fix the settings for the user after user confirming, or automatically. As a consequence, the surgeon may have less trouble achieving good image quality, in particular when working with FL signals. For example, with respect to the example above, a warning signal may be provided, informing the user that the working distance may be decreased to increase the quality of the FL image.

FIG. 3 shows a schematic diagram of an example of an overlay that is superimposed over a digital view of a surgical site. In the background of FIG. 3, the digital view on the surgical site is shown. On the right edge of the user interface, indicators 310-340 of a visual overlay are shown. For example, the visual overlay may comprise a round gauge 310 for indicating the suitability of the currently used settings, an indicator 320 indicating the suitability of the chosen illumination intensity, an indicator 330 indicating the intensity of the fluorescence emissions being recorded, and an indicator 340 indicating the suitability of the chosen working distance.

More details and aspects of the assistant for improving the use of the imaging device are mentioned in connection with the proposed concept or one or more examples described above or below (e.g. FIG. 1*a* to 2). The assistant may comprise one or more additional optional features corresponding to one or more aspects of the proposed concept or one or more examples described above or below.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Figure 4:
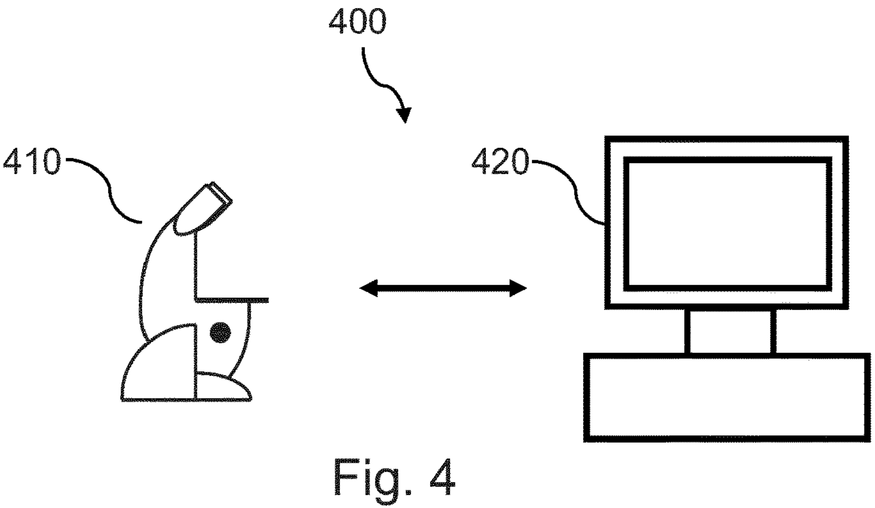
FIG. 4 shows a schematic diagram of a system comprising a imaging device and a computer system.

Some embodiments relate to a microscope, or more generally to an imaging device, imaging device comprising a system as described in connection with one or more of the FIGS. 1 to 3. Alternatively, a imaging device may be part of or connected to a system as described in connection with one or more of the FIGS. 1 to 3. FIG. 4 shows a schematic illustration of a system 400 configured to perform a method described herein. The system 400 comprises a microscope, or more generally imaging device 410 and a computer system 420. The microscope 410 is configured to take images and is connected to the computer system 420. The computer system 420 is configured to execute at least a part of a method described herein. The computer system 420 may be configured to execute a machine learning algorithm. The computer system 420 and microscope 410 may be separate entities but can also be integrated together in one common housing. The computer system 420 may be part of a central processing system of the microscope 410 and/or the computer system 420 may be part of a subcomponent of the microscope 410, such as a sensor, an actor, a camera or an illumination unit, etc. of the microscope 410.

The computer system 420 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 420 may comprise any circuit or combination of circuits. In one embodiment, the computer system 420 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 420 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 420 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 420 may also include a display device, one or more speakers, and a keyboard and/or controller, which can include a mouse, trackball, touch screen, voice-recognition device, or any other device that permits a system user to input information into and receive information from the computer system 420.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

Embodiments may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and/or training sequences (e.g. words or sentences) and associated training content information (e.g. labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model. The provided data (e.g. sensor data, meta data and/or image data) may be preprocessed to obtain a feature vector, which is used as input to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e. each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm (e.g. a classification algorithm, a regression algorithm or a similarity learning algorithm. Classification algorithms may be used when the outputs are restricted to a limited set of values (categorical variables), i.e. the input is classified to one of the limited set of values. Regression algorithms may be used when the outputs may have any numerical value (within a range). Similarity learning algorithms may be similar to both classification and regression algorithms but are based on learning from examples using a similarity function that measures how similar or related two objects are. Apart from supervised or semi-supervised learning, unsupervised learning may be used to train the machine-learning model. In unsupervised learning, (only) input data might be supplied and an unsupervised learning algorithm may be used to find structure in the input data (e.g. by grouping or clustering the input data, finding commonalities in the data). Clustering is the assignment of input data comprising a plurality of input values into subsets (clusters) so that input values within the same cluster are similar according to one or more (pre-defined) similarity criteria, while being dissimilar to input values that are included in other clusters.

Reinforcement learning is a third group of machine-learning algorithms. In other words, reinforcement learning may be used to train the machine-learning model. In reinforcement learning, one or more software actors (called "software agents") are trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards).

Furthermore, some techniques may be applied to some of the machine-learning algorithms. For example, feature learning may be used. In other words, the machine-learning model may at least partially be trained using feature learning, and/or the machine-learning algorithm may comprise a feature learning component. Feature learning algorithms, which may be called representation learning algorithms, may preserve the information in their input but also transform it in a way that makes it useful, often as a pre-processing step before performing classification or predictions. Feature learning may be based on principal components analysis or cluster analysis, for example.

In some examples, anomaly detection (i.e. outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g. a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g. be used to store, manipulate, or apply the knowledge.

Machine-learning algorithms are usually based on a machine-learning model. In other words, the term "machine-learning algorithm" may denote a set of instructions that may be used to create, train, or use a machine-learning model. The term "machine-learning model" may denote a data structure and/or set of rules that represents the learned knowledge (e.g. based on the training performed by the machine-learning algorithm). In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of its inputs (e.g. of the sum of its inputs). The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input.

Alternatively, the machine-learning model may be a support vector machine, a random forest model or a gradient boosting model. Support vector machines (i.e. support vector networks) are supervised learning models with associated learning algorithms that may be used to analyze data (e.g. in classification or regression analysis). Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

LIST OF REFERENCE SIGNS

- 100 Surgical imaging system, Surgical microscope system
- 110 System
- 105 Base unit
- 112 Interface
- 114 Processor
- 116 Storage device
- 120 Imaging device, microscope
- **130*a*** Ocular display
- **130*b*** Display
- 140 Arm
- 210 Determining a first set of settings
- 220 Determining a second set of settings
- 230 Providing a signal indicating a difference between the first and second set of settings
- 310 Round gauge
- 320 Indicator for suitability of illumination intensity
- 330 Indicator for intensity of the fluorescence emissions being recorded
- 340 Indicator for suitability of working distance
- 400 System
- 410 Microscope, Imaging device
- 420 Computer system

The invention claimed is:

1. A system for an imaging device of a surgical imaging system, the system comprising one or more processors and one or more storage devices, wherein the system is configured to:

track a progress of a surgical procedure;

determine a first set of settings being suitable for using the imaging device in the surgical procedure based on the progress of the surgical procedure;

determine a second set of settings currently being used; and provide a signal indicating a difference between the first and second set of settings, the signal comprising information on at least one setting to adjust to obtain the first set of settings.

2. The system according to claim 1, wherein the signal indicating the difference between the first and second set of settings is a display signal, the display signal comprising a visual representation of the information on the at least one setting to adjust to obtain the first set of settings.

3. The system according to claim 2, wherein the system is configured to provide a digital view on a surgical site as part of the display signal, with the digital view being based on imaging sensor data of an optical imaging sensor of the imaging device, and to provide the visual representation of the information on the at least one setting to adjust to obtain the first set of settings overlaid over the digital view.

4. The system according to claim 2, wherein the system is configured to determine an area of interest for the surgical procedure within the imaging sensor data, and to generate the display signal such, that the information on the at least one setting to adjust is shown outside the area of interest.

5. The system according to claim 1, wherein the progress of the surgical procedure comprises a plurality of steps, wherein the system comprises information on settings being suitable during the respective steps of the surgical procedure.

6. The system according to claim 1, wherein the system is configured to select an objective for determining the first set of settings according to the progress of the surgical procedure, and to determine the first set of settings based on the objective.

7. The system according to claim 6, wherein the system is configured to sweep values of one or more settings of the set of settings, and to evaluate the resulting optical performance in view of the objective, to determine the first set of settings.

8. The system according to claim 6, wherein the objective being selected relates to a quality of a representation of fluorescence emissions in imaging sensor data of an optical imaging sensor of the imaging device.

9. The system according to claim 1, wherein the first and second set of settings comprise one or more of the group of a working distance of the imaging device, an illumination provided by an illumination system of the surgical imaging system, a zoom level of the imaging device, and an aperture of the imaging device.

10. The system according to claim 1, wherein each set of settings comprises a first and a second subset of settings, wherein the system is configured to generate the signal indicating the difference between the first and second set of settings for the first subset of settings, and to automatically adjust the second subset of settings based on the first set of settings.

11. The system according to claim 1, wherein the system is configured to adapt the first set of settings using a machine-learning model being trained to reflect a preference of a specific surgeon.

12. The system according to claim 1, wherein the system is configured to track an activity of a surgeon using imaging sensor data of an optical imaging sensor of the imaging device, to detect a period of inactivity of the surgeon, and to provide the signal indicating the difference between the first and second set of settings when a period of inactivity of the surgeon is detected.

13. A surgical imaging system comprising an imaging device and the system according to claim 1.

14. The surgical imaging system according to claim 13, wherein the surgical imaging system is a surgical microscope system, and the imaging device is a microscope.

15. The surgical imaging system according to claim 13, wherein the surgical imaging system is a surgical endoscope system, and the imaging device is an endoscope.

16. The surgical imaging system according to claim 13, wherein the surgical imaging system is a surgical exoscope system and the imaging device is an exoscope.

17. A method for an imaging device of a surgical imaging system, the method comprising:

tracking a progress of a surgical procedure;

determining a first set of settings being suitable for using the imaging device in the surgical procedure based on the progress of the surgical procedure;

determining a second set of settings currently being used; and providing a signal indicating a difference between the first and second set of settings, the signal comprising information on at least one setting to adjust to obtain the first set of settings.

18. A non-transitory, computer readable medium comprising a program code for performing the method according to claim 17 when the computer program is executed on a processor.

* * * * *